(12) United States Patent
Mossanen-Shams et al.

(10) Patent No.: US 7,198,616 B2
(45) Date of Patent: Apr. 3, 2007

(54) MULTIPORT INFUSION DEVICE

(75) Inventors: Solmaz Mossanen-Shams, Bethesda, MD (US); Mir Mahmood Madani, Rossmoor, CA (US); Iden Mossanen-Shams, Uxbridge (GB)

(73) Assignee: Iden Mossanen-Shams (GB)

( * ) Notice: Subject to any disclaimer, the term of this patent is extended or adjusted under 35 U.S.C. 154(b) by 0 days.

(21) Appl. No.: 10/509,603

(22) PCT Filed: Mar. 28, 2003

(86) PCT No.: PCT/GB03/01377

§ 371 (c)(1),
(2), (4) Date: Sep. 27, 2004

(87) PCT Pub. No.: WO03/082396

PCT Pub. Date: Oct. 9, 2003

(65) Prior Publication Data

US 2005/0131353 A1    Jun. 16, 2005

Related U.S. Application Data

(60) Provisional application No. 60/368,560, filed on Apr. 1, 2002.

(51) Int. Cl.
*A61M 5/32* (2006.01)
(52) U.S. Cl. ..................... 604/174; 604/179
(58) Field of Classification Search ........... 604/174, 604/177, 179, 180, 284; 128/DIG. 6, DIG. 26
See application file for complete search history.

(56) References Cited

U.S. PATENT DOCUMENTS

| | | | | | |
|---|---|---|---|---|---|
| 2,261,213 | A | * | 11/1941 | Bierman | 604/179 |
| 2,449,882 | A | * | 9/1948 | Daniels | 604/179 |
| 3,782,378 | A | * | 1/1974 | Page | 128/888 |
| 3,782,382 | A | * | 1/1974 | Naftulin et al. | 604/6.09 |
| 3,939,832 | A | * | 2/1976 | Miller | 604/179 |
| 4,231,367 | A | * | 11/1980 | Rash | 604/165.02 |
| 4,311,137 | A | * | 1/1982 | Gerard | 604/28 |
| 4,316,461 | A | * | 2/1982 | Marais et al. | 604/179 |
| 4,586,919 | A | * | 5/1986 | Taheri | 604/9 |
| 4,666,434 | A | * | 5/1987 | Kaufman | 604/179 |
| 4,846,807 | A | * | 7/1989 | Safadago | 604/179 |
| 5,037,398 | A | * | 8/1991 | Buchanan | 604/180 |
| 5,263,943 | A | * | 11/1993 | Vanderbrook | 604/247 |
| 5,346,479 | A | * | 9/1994 | Schneider | 604/174 |
| 6,086,564 | A | * | 7/2000 | McLaughlin | 604/179 |
| 6,626,884 | B1 | * | 9/2003 | Dillon et al. | 604/409 |
| 2002/0120231 | A1 | * | 8/2002 | Douglas et al. | 604/82 |
| 2002/0177814 | A1 | * | 11/2002 | Meng et al. | 604/164.07 |

* cited by examiner

*Primary Examiner*—Sharon E. Kennedy
(74) *Attorney, Agent, or Firm*—Galgano & Associates, PLLC

(57) ABSTRACT

A multiport infusion device used as an intravenous administrator of prescribed fluid is provided. The device includes a band adapted to be secured to a user's body part near an intravenous therapy location. A multiport body is secured to the band and includes a multiport fluid exchange route fluidly communicating between a first port and at least a second port of the body's ports.

13 Claims, 2 Drawing Sheets

MULTIPORT INFUSION DEVICE

REFERENCES TO RELATED APPLICATIONS

This application is a U.S. national phase application based on application No. PCT/GB03/01377 filed on Oct. 9, 2003, which, in turn, claims the benefit of U.S. provisional application Ser. No. 60/368,560, filed Apr. 1, 2002.

FIELD OF THE INVENTION

The present invention generally relates to a multiport infusion device and, more particularly, to a device which reduces the risk of extravasation during the administration of intravenous fluids.

DESCRIPTION OF THE PRIOR ART

The skin and vein of a patient, whether an infant or an adult, receiving intravenous solutions can be damaged during the initial insertion of an intravenous needle. Similarly, the skin and vein of a patient can be damaged after the procedure by moving the intravenous lines, movement of the patient or by many other known factors. The injury can be caused due to the repeated application and or removal and unintended or inadvertent pulling of the tubes and the like, as well. This, in turn, displaces the needle in relation to the punctured skin site, thus causing damage and injury to the patient. The typical site of such damage includes the hand or arm of the patient, for example.

In known systems, the tube from the reservoir is directly coupled to the extension tube which, in turn, is coupled to the needle of the catheter, itself.

Normally, the intravenous catheter is secured to the patient's skin by an adhesive tape. A further safeguard is the creation of a 'loop' using part of the extended tubing circuit to form a loop and fixed to the skin by an adhesive tape. While the use of a loop can potentially reduce the risk of inadvertent pulls, it will not prevent such pulls and the needle may still be displaced by the movement of the patient or otherwise. Moreover, the use of tapes to secure the tubing can, itself, damage sensitive skin at the point of skin puncture. Indeed, some skin conditions are highly vulnerable to minor trauma brought about by any manipulation.

The prior art is replete with devices for intravenous tubing positioners and holders. However, none of the known devices isolate the extension tube and the reservoir tubing from each other totally. These known devices are also known to cause damage to the skin.

SUMMARY OF THE INVENTION

The scope of the invention is defined in the claims. What follows is a summary, only, of certain inventive features.

In a first aspect of the invention, a multiport infusion device used as an intravenous administrator of prescribed fluid is provided. The device includes a band adapted to be secured to a user's body part near an intravenous therapy location. A multiport body having at least two ports is further provided. The multiport body is secured to the band and includes a multiport fluid exchange route or conduit fluidly communication between a first port and at least a second port.

In embodiments, the band is a flexible band. The first port may accommodate an extension tube extending from a needle and the at least second port may accommodate an intravenous tube in fluid communication with the extension tube. The at least two ports may be three ports or more ports, each one of them may include a sealing cap. The band includes an adjustment mechanism, which may be a plurality of adjustment holes and a fastening device communicating with the adjustment holes. The band may lie flush with the skin, when in use; whereas the multiport body is raised from the band allowing air circulation between a tube extending from one of the at least two ports and the intravenous therapy location.

In another aspect of the invention, the multiport infusion device includes a flexible band having a first end and a second end and adapted to be secured to a user's body part near an intravenous therapy location. A fastening device is positioned on the flexible band for fastening the flexible band to the user's body part. A main body has a three-way fluid exchange route or conduit, each route or conduit of the three way fluid exchange route or conduit has an opening port. the opening port has a sealing cap adapted to seal the port.

In embodiments of another aspect of the invention, the main body is raised from the flexible band allowing air circulation between a tube extending from one of the ports of the three-way fluid exchange route or conduit and the intravenous therapy location. The flexible band includes an adjustment mechanism including the fastening device. A plurality of adjustment holes along the flexible band may be provided for communicating with the fastening device. The flexible band may include means for preventing rotation of the band about the user when placed on the user.

In another aspect of the invention, the multiport infusion device includes a band and means for providing fluid communication routes between an extension tube and at least another tube. Also included is means for preventing rotation of the band.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The present embodiment is directed to an intravenous device and, more particularly, to an intravenous device which reduces the risk of extravasation during the administration of intravenous fluids. The intravenous device is, in embodiments, a bracelet positioned about the limb or other body part of the user. A peripheral IV is inserted into the device and will act as a 'safe' buffer between the extension and reservoir tubes connected to an angiocath, for example. The intravenous device requires no modification to the currently used reservoir and extension tubes, nor do any known phlebotomy techniques need to be altered.

The device prevents catheter displacements caused by pulls of the tubes secondary to a patient's position change or movements of the IV pole. The use of the intravenous device also directly reduces pressure exerted to the lines and reduces the risk of injuries caused by movements of the limbs or inadvertent displacement of the catheter. Additionally, disengagement and/or exchange of tubing system are greatly simplified. The device also provides additional infusion ports, allowing less manipulation of the tubing and potential dislodgment thereof.

Figure 1:
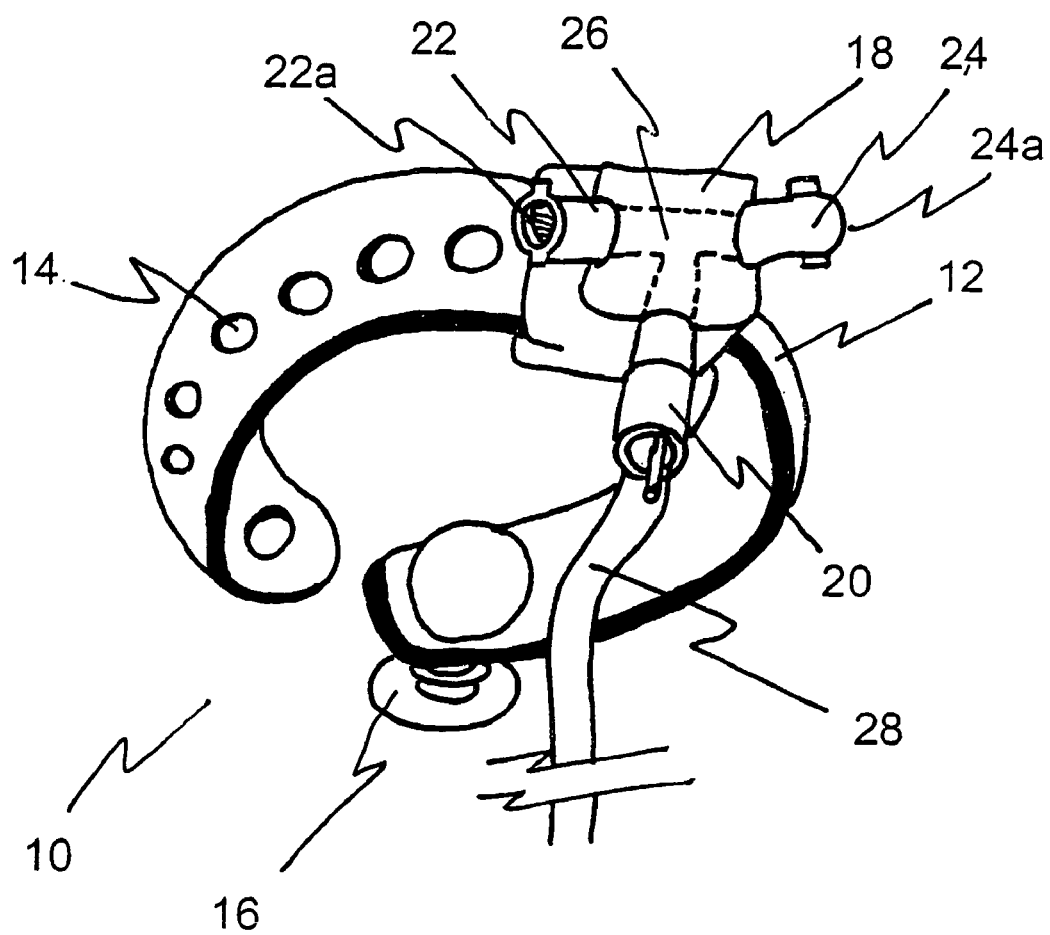
FIG. 1 shows a perspective view of the present invention.

Referring now to FIG. 1, the intravenous device is generally depicted by reference numeral 10. The intravenous device 10 includes a band 12, which may be made from a flexible and elastic type material to securely fit over a user's wrist or other portion of any limb or body part. In one embodiment, the band 12 includes adjustment holes 14 communicating with a rivet type device, button or other fastening device 16 placed near or at an end of the band itself. Other fastening or coupling devices may equally be used in order to securely fit the intravenous device 10 on the user. For example, a tension band or other device may be used.

Still referring to FIG. 1, a body 18 having multiple ports 20, 22 and 24 in fluid communication with one another via fluid path 26 is provided on the band 10. In an embodiment, the ports 22 and 24 are positioned substantially at a perpendicular angle to the port 20, and may include caps 22a and 24a, respectively, to seal the ports 22 and 24. The port 20 may also, in embodiments, have a sealing cap. In FIG. 1, the caps 22a and 24a are sealing the ports 22 and 24. However, in use, one or both of the caps 22a and 24a can be removed in order to accommodate a tube. The port 20 is preferably used for an extension tube 28 connected to an intravenous needle (not shown). In embodiments more or less than the two additional ports 22 and 24 is also contemplated.

Figure 2:
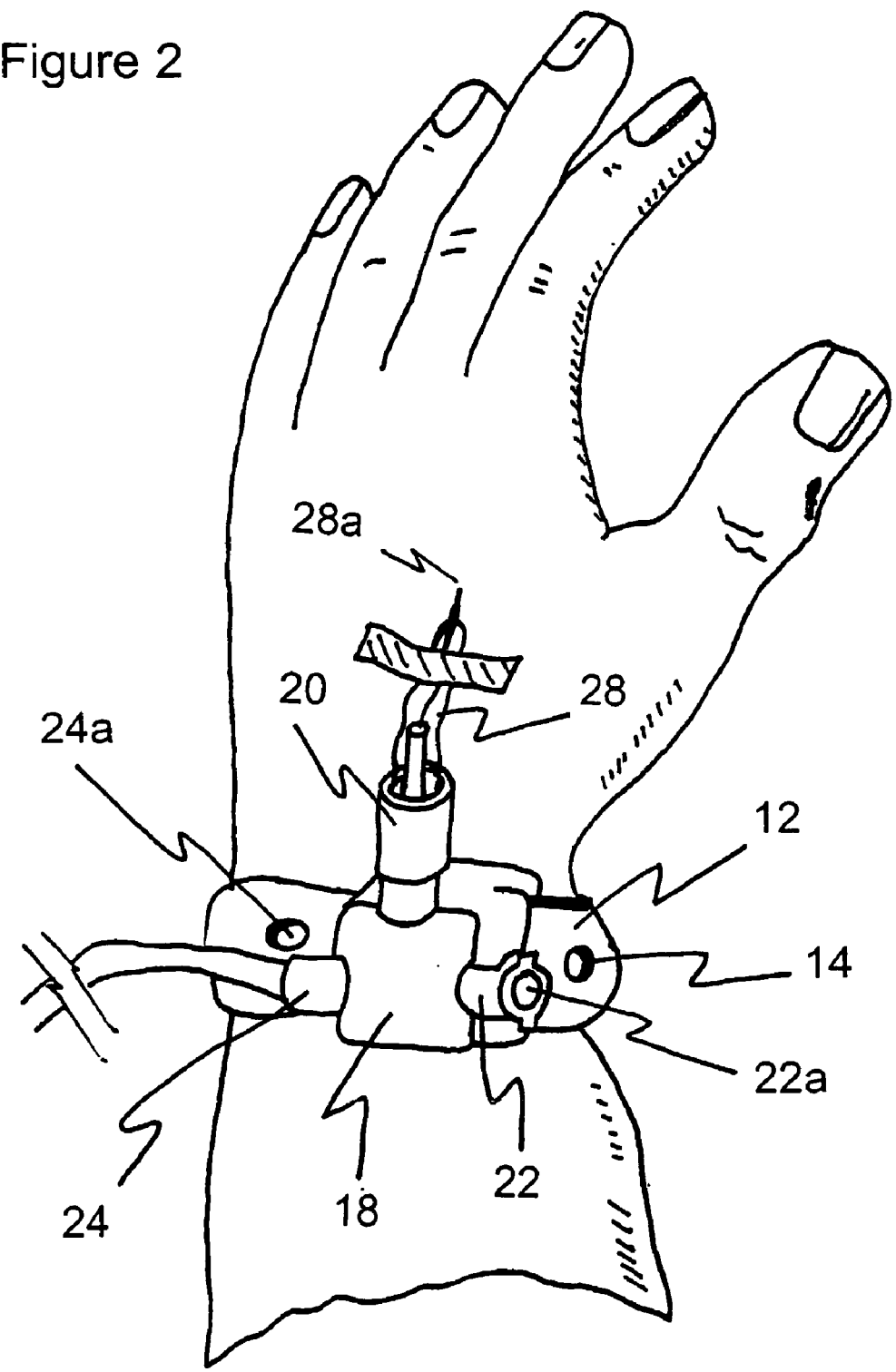
FIG. 2 shows an illustrative example of the present invention about a user's wrist.

FIG. 2 shows the band attached to a user's wrist. This is only one illustrative example and should not be deemed a limiting factor, in any way, of the present invention. As seen in FIG. 2, the adjustment mechanism securely fits the band 12 to the user's wrist and prevents rotation thereof. Also, the body 18 is raised from the band allowing air circulation between the tube 28 extending from the port 20 and the intravenous therapy location. This prevents movement of any of the tubes, for example, tube 28 or dislodgment of the needle 28a. In the embodiment shown in FIG. 2, the cap 24a is open and the cap 22a remains closed, sealing the port 22. A tube may extend from the port 24 and would thus be in fluid communication with the tube 28 via the fluid communication path 26. The tube connected to the port 24 is used for infusion, as can be a tube connected to port 22. The tubes are isolatable from one another, i.e. can be unplugged individually from their respective ports.

Other aspects and features of the present invention can be obtained from a study of the drawings, the disclosure and the appended claims.

In this description of the invention the intended use of the device is described, for convenience, in relation to the intravenous administration of fluids. It is implicit, of course, that the device may conveniently be used to anchor any flexible connection made between an external device and a point of entry into a human or animal body. For example, the device may be used to anchor naso-gastric tubes, urinary catheters and drain tubes such as chest drains. The term 'intravenous' as used in the description and claims of this application should, therefore, be construed in the broad sense of 'into the body'.

Also for convenience, the description describes the device as being secured 'to a user's body part'. It is clear that the intended use of the device is to prevent damage at the site of entry of the flexible connection into the body. Therefore, in some circumstances, such as where a patient is immobile, it may be equally appropriate to secure the device to a fixed point relative to the patient. Such a fixed point may conveniently be a chair or wheelchair in which a patient is sitting, or a bed in which a patient is lying. References to the term 'user's body part' in the description and claims should therefore be construed in the broad sense of a fixed point relative to the site of entry of a flexible tube into the patient's body.

The invention claimed is:

1. A multiport infusion device to be used as an intravenous administrator of prescribed fluid, comprising:
   a band adapted to be secured to a user's body part near an intravenous therapy location having a first strap having a first strap end and a second strap having a second strap end; and
   a multiport body secured to and disposed adjacent to said band and an upper surface on which are mounted a plurality of ports for connecting tubes, said multiport body having a substantially flat bottom surface and a pair of regions in each of which one of said straps enter and against each of which one of said strap ends is anchored, said regions projecting from said bottom surface of said body so that when said band is secured to a user's body, said band encircles the whole of the user's limb and said regions lift portions of said straps adjacent to said body from the encircled limb as the strap enters said body.

2. The multiport infusion device according to claim 1, wherein said multiport body is in the form of a block.

3. The multiport infusion device according to claim 1, wherein said multiport body is of substantially constant cross-section.

4. The multiport infusion device according to claim 1, wherein said multiport body is raised from said band allowing air circulation between a tube extending from one of the ports and said intravenous therapy location.

5. The multiport infusion device according to claim 2, wherein at least one other major surface of said multiport body aside from said bottom surface thereof is also substantially flat.

6. The multiport infusion device according to claim 5, wherein each other major surface of said multiport body aside from said bottom surface is also substantially flat.

7. The multiport infusion device, according to claim 1, wherein said multiport body having at least two ports, at least one of which ports is provided with a sealing cap.

8. The multiport infusion device according to claim 7, wherein said cap is incorporated into one of said ports.

9. The multiport infusion device according to claim 1, wherein said multiport body includes check valve-less fluid flow passages within said multiport body.

10. The multiport infusion device according to claim 1, wherein said multiport body has a fluid communication path arranged in a T-shaped pattern.

11. The multiport infusion device according to claim 1, wherein said multiport body has a first port and second port and a fluid exchange conduit between said first and second port of said multiport body.

12. A multiport infusion device to be used as an intravenous administrator of prescribed fluid, comprising:
   a band adapted to be secured to a user's body part near an intravenous therapy location; and
   a multi port body secured to and disposed adjacent to said band, said multiport body having a substantially flat bottom surface and an upper surface on which are mounted a plurality of ports for connecting tubes, said band being designed to encircle the whole of said user's body part and, when in use, said band holds the bottom surface of said multiport body directly against the surface of said user's body part.

13. The multiport infusion device according to claim 12, wherein said multiport body has a fluid communication path arranged in a T-shaped pattern.

* * * * *